(12) United States Patent
Iwasawa et al.

(10) Patent No.: US 6,403,841 B1
(45) Date of Patent: Jun. 11, 2002

(54) PROCESS FOR PREPARING PARTIAL OXIDATES OF LOWER ALCOHOLS

(75) Inventors: Yasuhiro Iwasawa; Youzhu Yuan; Takafumi Shido, all of Tokyo; Nobuhiro Tamura, Yokosuka, all of (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 09/856,303
(22) PCT Filed: Sep. 19, 2000
(86) PCT No.: PCT/JP00/06380

§ 371 (c)(1),
(2), (4) Date: Jul. 24, 2001

(87) PCT Pub. No.: WO01/21566
PCT Pub. Date: Mar. 29, 2001

(30) Foreign Application Priority Data

Sep. 22, 1999 (JP) ............................................ 11-269480

(51) Int. Cl.$^7$ .......................... C07C 43/30; C07C 41/00
(52) U.S. Cl. ...................................... 568/594; 568/671
(58) Field of Search ................................. 568/594, 671

(56) References Cited

FOREIGN PATENT DOCUMENTS

| DE | 800 399 | 10/1950 |
|---|---|---|
| DE | 1 155 780 | 10/1963 |
| DE | 1 177 126 | 9/1964 |
| JP | 47-29309 | 11/1972 |
| JP | 48-63983 | 9/1973 |
| JP | 58-162546 | 9/1983 |
| JP | 2-115042 | 4/1990 |
| JP | 4-356436 | 12/1992 |
| JP | 05-237387 | 9/1993 |
| JP | 06-065123 | 3/1994 |

*Primary Examiner*—Samuel Barts
*Assistant Examiner*—Elvis O. Price
(74) *Attorney, Agent, or Firm*—Venable; Robert Kinberg

(57) ABSTRACT

An object of the present invention is to provide a catalyst for a lower alcohol oxidation reaction which makes possible to manufacture a partial oxide of a lower alcohol such as dimethoxymethane or the like selectively and efficiently by direct oxidation of a lower alcohol such as methanol or the like, and to provide a method for manufacturing a partial oxide of a lower alcohol such as dimethoxymethane or the like selectively and efficiently from a lower alcohol such as methanol or the like by using this catalyst for a lower alcohol oxidation reaction. A partial oxide of a lower alcohol such as dimethoxymethane or the like is manufactured by subjecting a lower alcohol to vapor phase contact oxidation with a molecular oxygen-containing gas in the presence of an oxidation reaction catalyst for a lower alcohol composed of a rhenium-antimony compound oxide such as $SbRe_2O_6$ or the like. When the vapor phase contact oxidation is conducted, in particular, at a temperature of 300 to 400° C., dimethoxymethane can be manufactured highly selectively.

5 Claims, 1 Drawing Sheet

PROCESS FOR PREPARING PARTIAL OXIDATES OF LOWER ALCOHOLS

TECHNICAL FIELD

This invention relates to a catalyst for a lower alcohol oxidation reaction such as a catalyst for a methanol oxidation reaction or the like whose active component is $SbRe_2O_6$ or other such rhenium-antimony compound oxides, and to a manufacturing method for a partial oxide of a lower alcohol such as dimethoxymethane or the like from methanol or other such lower alcohols using the catalyst for a lower alcohol oxidation reaction.

BACKGROUND ART

Dimethoxymethane has been conventionally manufactured by subjecting methanol and formaldehyde as materials to reaction in aqueous solution with an acidic catalyst. The examples of the acidic catalyst used in such reaction include mineral acids such as hydrochloric acid, sulfuric acid and the like, Lewis acid such as $FeCl_3$, $AlCl_3$ and the like, overacidic cation exchange resin, and inorganic solid acid and the like (German Patent Specification Nos. 800399, 1177126 and 1155780, Japanese Laid-Open Patent Application Nos. 47-29309 and 58-162546). However, the material formaldehyde is prepared by oxidizing methanol, so that the above-mentioned method has two-stage process wherein formaldehyde which is prepared from methanol is subjected to reaction with methanol, and it causes a problem in its productivity.

On the other hand, a method in which dimethoxymethane is directly manufactured from methanol without using formaldehyde is also known. The examples of the method include a method using a catalyst containing a copper oxide (Japanese Laid-Open Patent Application No. 5-237387), a method using a catalyst in which metal comprised of two different kinds of metal and/or compounds of these metals exist on the ion conductor (Japanese Laid-Open Patent Application No. 6-65123). However, the method for manufacturing dimethoxymethane using the former catalyst containing a copper oxide takes a long time to complete the reaction, and the yield is not necessarily satisfactory, while the method for manufacturing dimethoxymethane using the latter catalyst shows high selectivity of methyl formate, though it shows selectivity as low as 7% with regard to dimethoxymethane. Both methods have had problems to be solved in the aspect of practicability.

Dimethoxymethane is also called formaldehyde dimethyl acetal or methylal, and known as a useful compound mainly used as a material of medicines, flavorings and resin. A solid catalyst which can manufacture such useful compounds selectively and efficiently by direct methanol oxidation has not been known yet. An object of the present invention is to provide a catalyst for a lower alcohol oxidation reaction which makes possible to manufacture a partial oxide of a lower alcohol such as dimethoxymethane or the like selectively and efficiently by direct oxidation of a lower alcohol such as methanol or the like, and to a method for manufacturing a partial oxide of a lower alcohol such as dimethoxymethane or the like selectively and efficiently from a lower alcohol such as methanol or the like by using this catalyst for a lower alcohol oxidation reaction.

DISCLOSURE OF THE INVENTION

The inventors conducted diligent research aimed at achieving the stated object, learned that a catalyst which has $SbRe_2O_6$ or other rhenium-antimony compound oxides as active components shows excellent catalytic activity in oxidation reaction of methanol or other lower alcohol, and that dimethoxymethane or other partial oxide of a lower alcohol can be manufactured selectively and efficiently with this rhenium-antimony compound oxide catalyst, and the present invention has been completed.

Specifically, the present invention relates to a method for manufacturing a partial oxide of a lower alcohol characterized by that a lower alcohol is subjected to vapor phase contact oxidation with a molecular oxygen-containing gas in the presence of a lower alcohol oxidation reaction catalyst which has a rhenium-antimony compound oxide as its active component, a method for manufacturing a partial oxide of a lower alcohol, wherein the rhenium-antimony compound oxide is $SbRe_2O_6$, a method for manufacturing a partial oxide of a lower alcohol, wherein vapor phase contact oxidation is conducted at a temperature of 300–400° C., a method for manufacturing a partial, oxide of a lower alcohol, wherein a lower alcohol is methanol, and a method for manufacturing a partial oxide of a lower alcohol, wherein a partial oxide of a lower alcohol is dimethoxymethane.

The present invention also relates to a catalyst for a lower alcohol oxidation reaction characterized in having a rhenium-antimony compound oxide as its active component, a catalyst for a lower alcohol oxidation reaction, wherein the rhenium-antimony compound oxide is $SbRe_2O_6$, and a catalyst for a lower alcohol oxidation reaction, wherein the lower alcohol is methanol.

BEST MODE FOR CARRYING OUT THE INVENTION

Figure 1:
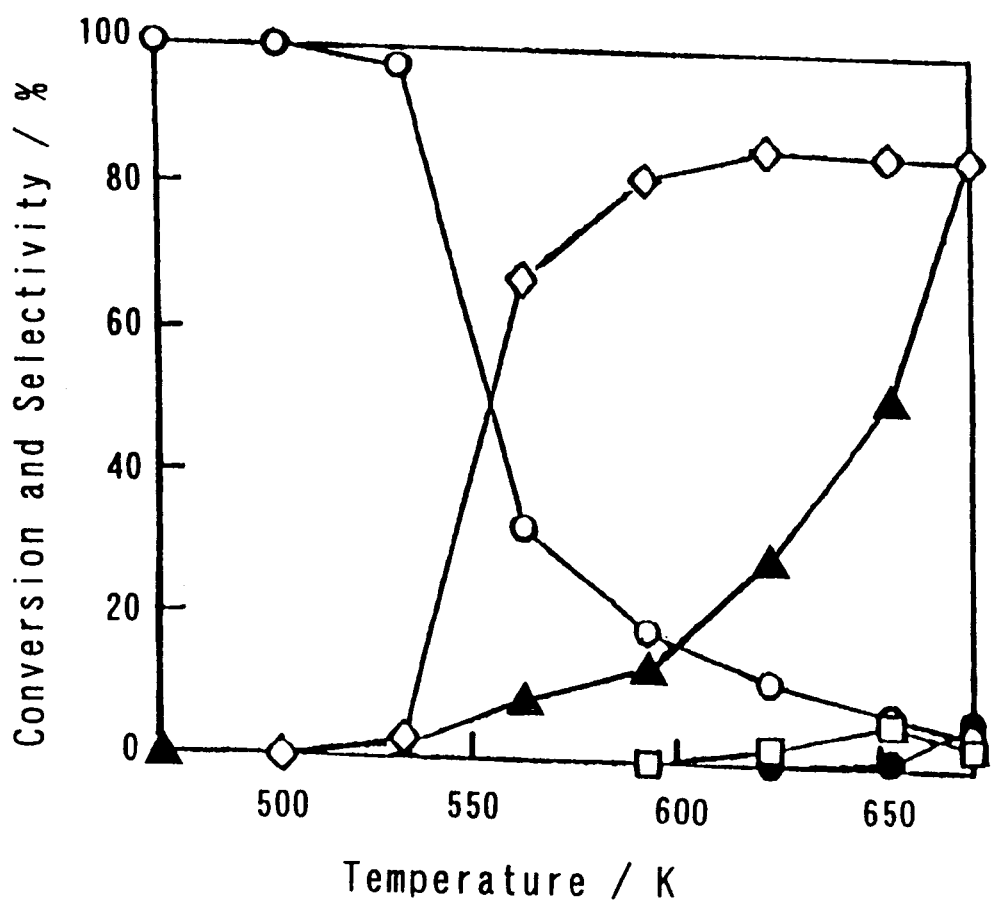
FIG. 1 is a graph of the effect that reaction temperature has on the conversion of methanol and the selectivity of the products such as dimethoxymethane or the like in a methanol oxidation reaction using the $SbRe_2O_6$ catalyst of the present invention.

The catalyst of the present invention for oxidation reaction of a lower alcohol such as methanol or the like is not limited particularly as long as it has a rhenium-antimony compound oxide as its active component, and the examples of the catalyst for a lower alcohol oxidation reaction include rhenium-antimony compound oxides such as $SbRe_2O_6$, $SbReO_4 \cdot 2H_2O$ and the like, and other materials which contain other metals or oxides of these metals to the extent that the catalytic activity thereof is not compromised. However, $(NH_4)ReO_4$ or other rhenium oxides, $Sb_2O_3$ or other antimony oxides, and $(NH_4)ReO_4 + Sb_2O_3$ created by mixing $(NH_4)ReO_4$ or other rhenium oxides and $Sb_2O_3$ or other antimony oxides physically are not included in the catalysts of the present invention for oxidation reaction of a lower alcohol. For example, though a rhenium oxide such as $(NH_4)ReO_4$ or the like shows a lower alcohol oxidation reaction activity, the ratio of producing a perfect oxide such as carbon dioxide or the like is high, whereas an antimony oxide such as $Sb_2O_3$ or the like hardly shows lower alcohol oxidation reaction activity.

$SbRe_2O_6$, a rhenium-antimony compound oxide, can be synthesized, for example, by solid phase reaction between $SbReO_4 \cdot 2H_2O$ and metal rhenium, and examples of shapes of such solid catalysts having compound oxides made from antimony and rhenium such as $SbRe_2O_6$ or the like as active component include powder, granular, pellet, spherical, and honeycomb. Further, a rhenium-antimony compound oxide can be carried by various kinds of carriers, and such carriers are not limited as long as they are usually used when active component of a catalyst is being carried. The examples of the carrier include clay minerals such as activated carbon, silica, alumina, silica-alumina, zeolite, bentonite and the like; inorganic carriers such as magnesia, silica-magnesia, titania, zirconia and the like; organic carriers such as ion exchange resin, chelating resin and the like.

A method for manufacturing a partial oxide of a lower alcohol of the present invention is characterized by that a lower alcohol is subjected to vapor phase contact oxidation with a molecular oxygen-containing gas in the presence of a lower alcohol oxidation reaction catalyst which has a rhenium-antimony compound oxide such as $SbRe_2O_6$ or the like as its active component. A lower alcohol in the present invention refers to alcohol having 1~4 carbon atoms, that is, methanol, ethanol, propanol and butanol. Among them, it is preferable to use methanol in consideration of the alcohol conversion. Specific examples of a partial oxide of a lower alcohol of the present invention include dialkoxymethane such as dimethoxymethane and the like and dialkyl ether such as dimethyl ether and the like.

Examples of the molecular oxygen-containing gas in the present invention include pure oxygen gas, air, and other such oxygen-containing gases. The vapor phase contact oxidation in the presence of a catalyst for a lower alcohol oxidation reaction of the present invention can be carried out by introducing a raw material gas composed of a mixed gas in which a molecular oxygen-containing gas and a diluent gas have been added to a lower alcohol, into a fixed bed reactor containing the above-mentioned catalyst. Examples of the diluent gas include nitrogen, carbon dioxide, a rare gas such as helium, argon and the like, an inert gas such as water vapor and the like, and mixtures of these gases.

The concentrations of a lower alcohol such as methanol or the like and of oxygen in the oxidation reaction of a lower alcohol such as methanol or the like using a catalyst for a lower alcohol oxidation reaction of the present invention are not limited particularly as long as they do not lower the production efficiency of a partial oxide of a lower alcohol such as dimethoxymethane or the like, which is the object of the reaction. Though the reaction temperature in the oxidation reaction depends on the kind of a lower alcohol used as a material, and of a partial oxide of a lower alcohol, which is the object of the reaction, when dimethoxymethane is manufactured by partial oxidation of methanol, for example, the selectivity of nearly 90% could be attained at the reaction temperature of 300~400° C.

The present invention will now be described in more specific terms through examples, but the technological scope of the present invention is not limited to these examples. Various kinds of products of methanol oxidation are used as examples here, and the conversion and selectivity referred to in the examples are expressed by the following equations.

Methanol conversion=(moles of reacted methanol)/(moles of supplied methanol)×100

Dimethoxymethane selectivity=(moles of produced dimethoxymethane)×3/(moles of reacted methanol)×3×100

Formaldehyde selectivity=(moles of produced formaldehyde)/(moles of reacted methanol)×100

Dimethyl ether selectivity=(moles of produced dimethyl ether)/(moles of reacted methanol)×2×100

Methyl formate selectivity=(moles of produced methyl formate)/(moles of reacted methanol)×2×100

Formic acid selectivity=(moles of produced formic acid)/(moles of reacted methanol)×100

Carbon oxide selectivity=(moles of produced carbon oxide)/(moles of reacted methanol)×100

Carbon dioxide selectivity=(moles of produced carbon dioxide)/(moles of reacted methanol)×100

REFERENCE 1

Preparation of Rhenium-antimony Compound Oxides 2.8 g of rhenium(VII) oxide ($Re_2O_7$; made by Soekawa; purity: 99.99%) was put in a Teflon autoclave, and 2 ml of deionized water was added. 1.7 g of antimony(III) oxide ($Sb_2O_3$; made by Soekawa, purity: 99.99%) was added to this at room temperature under vigorous stirring, after which the autoclave was sealed and the contents were heated for 24 hours at 200° C., then aged for another 6 days at room temperature. The sample thus obtained was dried under reduced pressure, which yielded $SbOReO_4 \cdot 2H_2O$. This $SbOReO_4 \cdot 2H_2O$ was spray dried and pre-calcined, rhenium (Re) was added, and this mixture was calcined at 500° C., which yielded a compound oxide catalyst of $SbRe_2O_6$. The crystal structure, valence, and oscillation mode were then analyzed using an X-ray diffraction apparatus (made by Rigaku), an X-ray photoelectron spectroscope (made by Rigaku), and a Raman spectroscope (made by JASCO Corporation), which confirmed that the obtained compound was an rhenium-antimony compound oxide of $SbRe_2O_6$.

EXAMPLE 1

Methanol Oxidation Reaction

A quartz reaction tube was packed with 0.2 g of the catalyst for a methanol oxidation reaction composed of $SbRe_2O_6$ prepared in Reference 1. After the catalyst was pretreated with a mixed gas of $He/O_2$ at 400° C., a mixed gas composed of 5 vol% methanol, 10 vol% oxygen, and 85 vol% helium was introduced into the reaction tube at a velocity of 34 ml/min (GHSV=10,000/h), and a methanol oxidation reaction was conducted. This methanol oxidation reaction using the flow reactor was conducted at various reaction temperatures shown in FIG. 1. As gas chromatography columns, Polapack-N (2.5m) was used for separation and quantitation of methanol as a material, and dimethyl ether, dimethoxymethane, formaldehyde and methyl formate as the products of the reaction, and Unibeads C (2m) was used for separation and quantitation of CO and $CO_2$ as the products of the reaction respectively, and analysis was conducted at column temperature of 413K (140° C.).

Methanol conversion (△) and selectivities of dimethoxymethane (◇), dimethyl ether (○), formaldehyde (●) and methyl formate (□) were calculated at each of various temperatures from the results of this analysis of the above-mentioned reaction products and the like using the equations given above. These results are shown in FIG. 1. It can be seen from these results that when the reaction temperature was 550K (277° C.) or lower, methanol conversion was low (5% or lower) and the main product of the reaction was dimethyl ether, and that when the reaction temperature was over 550K (277° C.), methanol conversion and dimethoxymethane selectivity increased and dimethyl ether selectivity decreased, and that when the reaction temperature was over 623K (350° C.), dimethoxymethane selectivity showed constant values of scant 90%, and that carbon dioxide and carbon oxide were not produced at all.

EXAMPLE 2

Methanol Oxidation Reaction

The methanol oxidation reaction was conducted in the same manner as in Example 2 except that $SbRe_2O_6$ catalyst and $SbOReO_4 \cdot 2H_2O$ catalyst were pretreated with helium gas at 300° C. for 1 hour while the reaction being conducted at 320° C., and methanol conversion and selectivities of dimethoxymethane, formaldehyde, dimethyl ether, methyl formate, formic acid, carbon dioxide and carbon oxide were calculated respectively. As a reference, the reaction was conducted in the same manner with $(NH_4)ReO_4+Sb_2O_3$, a catalyst created by physical mixing of $(NH_4)ReO_4$ and $Sb_2O_3$, and methanol conversion and selectivity of the reaction products were calculated. These results are given in Table 1.

TABLE 1

| Catalyst | $CH_3OH$ Conversion (%) | Selectivity (%) | | | | | | |
|---|---|---|---|---|---|---|---|---|
| | | $(CH_3O)_2CH_2$ | HCHO | $CH_3OCH_3$ | $HCOOCH_3$ | HCOOH | $CO_2$ | CO |
| $SbRe_2O_6$ | 12.3 | 89.0 | 0 | 11.0 | 0 | 0 | 0 | 0 |
| $SbOReO_4 \cdot 2H_2O$ | 4.7 | 1.0 | 0 | 99.0 | 0 | 0 | 0 | 0 |
| $(NH_4)ReO_4 + Sb_2O_3$ | 1.3 | trace | 0 | ~100 | 0 | 0 | 0 | 0 |

It can be seen from Table 1 that $SbRe_2O_6$ catalyst and $SbOReO_4 \cdot 2H_2O$ catalyst have methanol oxidation reaction activity and in particular, high selectivity of dimethoxymethane can be achieved by using $SbRe_2O_6$ as a catalyst, on the contrary, the reaction hardly showed any progress with $(NH_4)ReO_4+Sb_2O_3$, a catalyst created by physical mixing of $(NH_4)ReO_4$ or other rhenium oxide and $Sb_2O_3$ or other antimony oxide. From the above results, it has been found that catalytic activity is not expressed by mixing antimony oxides and rhenium oxides simply, and that catalytic activity is greatly dependent on the composition and the structure of rhenium-antimony compound oxides.

INDUSTRIAL APPLICABILITY

The present invention involves the use of $SbRe_2O_6$ or other rhenium-antimony compound oxides as a catalyst for oxidation reaction of a lower alcohol such as methanol or the like, which allows a partial oxide of a lower alcohol such as dimethoxymethane or the like to be manufactured selectively and efficiently from a lower alcohol such as methanol or the like.

What is claimed is:

1. A method for manufacturing a partial oxide of a lower alcohol characterized by that a lower alcohol is subjected to vapor phase contact oxidation with a molecular oxygen-containing gas in the presence of a lower alcohol oxidation reaction catalyst which has a rhenium-antimony compound oxide as its active component.

2. A method for manufacturing a partial oxide of a lower alcohol according to claim 1, wherein a rhenium-antimony compound oxide is $SbRe_2O_6$.

3. A method for manufacturing a partial oxide of a lower alcohol according to claim 1, wherein vapor phase contact oxidation is conducted at a temperature of 300~400° C.

4. A method for manufacturing a partial oxide of a lower alcohol according to claim 1, wherein a lower alcohol is methanol.

5. A method for manufacturing a partial oxide of a lower alcohol according to claim 1, wherein a partial oxide of a lower alcohol is dimethoxymethane.

* * * * *